US011649424B2

(12) United States Patent
Vunjak-Novakovic et al.

(10) Patent No.: US 11,649,424 B2
(45) Date of Patent: May 16, 2023

(54) SMART MICRO BIOREACTOR PLATFORM FOR HIGH THROUGHPUT MECHANICAL STIMULATION OF CARDIAC MICROTISSUE

(71) Applicant: The Trustees of Columbia University in the City of New York, New York, NY (US)

(72) Inventors: Gordana Vunjak-Novakovic, New York, NY (US); Hesam Parsa, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 732 days.

(21) Appl. No.: 16/043,877

(22) Filed: Jul. 24, 2018

(65) Prior Publication Data
US 2019/0031991 A1     Jan. 31, 2019

Related U.S. Application Data

(60) Provisional application No. 62/538,014, filed on Jul. 28, 2017.

(51) Int. Cl.
 *C12M 1/32* (2006.01)
 *C12M 1/34* (2006.01)
 (Continued)

(52) U.S. Cl.
 CPC ............ *C12M 21/08* (2013.01); *C12M 23/12* (2013.01); *C12M 23/16* (2013.01); *C12M 35/04* (2013.01); *C12M 41/40* (2013.01); *C12N 5/0068* (2013.01)

(58) Field of Classification Search
 CPC ...... C12M 21/08; C12M 23/12; C12M 23/16; C12M 35/04; C12M 41/40; C12N 5/0068
 (Continued)

(56) References Cited

U.S. PATENT DOCUMENTS 4,789,601 A * 12/1988 Banes ................... C12M 23/20
                                                                              428/116
6,218,182 B1    4/2001 Naughton et al.
(Continued)

FOREIGN PATENT DOCUMENTS

WO    2013086486 A1    12/2012
WO    2013184527        12/2013
(Continued)

OTHER PUBLICATIONS

International Search Report and Written Opinion cited in corresponding International Application No. PCT/US19/43722 dated Oct. 16, 2019.
(Continued)

*Primary Examiner* — Liban M Hassan
(74) *Attorney, Agent, or Firm* — Reed Smith LLP; Lisa A. Chiarini; Walter M. Egbert, III

(57) ABSTRACT

The present disclosure relates to a pneumatic microfluidic platform for high-throughput studies of cardiac hypertrophy that enables repetitive (hundreds of thousands of times) and robust (over several weeks) manipulation of cardiac μtissues. The platform is reusable for stable and reproducible mechanical stimulation of cardiac μtissues (each containing only 500 cells). Heterotypic and homotypic μtissues produced in the device were pneumatically loaded in a range of regimes, with real-time on-chip analysis of tissue phenotypes. Concentrated loading of the three-dimensional cardiac tissue faithfully recapitulated the pathology of volume overload seen in native heart tissue. Sustained volume overload of μtissues was sufficient to induce pathological cardiac remodeling associated with upregulation of the fetal gene program, in a dose-dependent manner.

16 Claims, 5 Drawing Sheets
Specification includes a Sequence Listing.

(51) Int. Cl.
  *C12M 3/00* (2006.01)
  *C12N 5/00* (2006.01)
  *C12M 3/06* (2006.01)
  *C12M 1/42* (2006.01)

(58) Field of Classification Search
  USPC .......................................... 435/286.6, 289.1
  See application file for complete search history.

(56) References Cited

U.S. PATENT DOCUMENTS

| | | | |
|---|---|---|---|
| 6,979,308 | B1 | 12/2005 | MacDonald et al. |
| 7,198,940 | B2 | 4/2007 | Vellinger et al. |
| 7,604,987 | B2 | 10/2009 | Hutmacher et al. |
| 8,492,140 | B2 | 7/2013 | Smith et al. |
| 8,748,180 | B2 | 6/2014 | Shuler et al. |
| 2004/0132184 | A1 | 7/2004 | Dennis et al. |
| 2007/0038384 | A1 | 2/2007 | Kirk et al. |
| 2011/0250585 | A1 | 10/2011 | Ingber et al. |
| 2014/0094388 | A1 | 4/2014 | Wakatsuki |
| 2014/0335496 | A1 | 11/2014 | Grego et al. |
| 2015/0087004 | A1 | 3/2015 | Chen et al. |
| 2016/0015860 | A1 | 1/2016 | Murry et al. |
| 2016/0130555 | A1 | 5/2016 | Ruohola-Baker et al. |
| 2016/0201037 | A1 | 7/2016 | Tuan et al. |
| 2017/0016875 | A1 | 1/2017 | Parker et al. |
| 2017/0226457 | A1 | 8/2017 | Mosig et al. |
| 2017/0227525 | A1 | 8/2017 | Griffith et al. |

FOREIGN PATENT DOCUMENTS

| | | |
|---|---|---|
| WO | 2014085933 | 6/2014 |
| WO | 2014085933 A1 | 6/2014 |
| WO | 2014201254 | 12/2014 |
| WO | 2015013210 A1 | 1/2015 |
| WO | 2015054383 | 4/2015 |
| WO | 2015061907 | 5/2015 |
| WO | 2015084168 | 6/2015 |
| WO | 2016004394 A1 | 1/2016 |
| WO | 2016174607 A1 | 11/2016 |
| WO | 2016183143 A1 | 11/2016 |
| WO | 2016191179 A1 | 12/2016 |
| WO | 2017059173 A1 | 4/2017 |
| WO | 2018052953 A1 | 9/2017 |
| WO | 2018071354 A1 | 10/2017 |
| WO | 2018090035 A1 | 11/2017 |

OTHER PUBLICATIONS

Leong KW, "Integrated microphysiological system of cerebral organoid and blood vessel for disease modeling and neuropsychiatric drug screening", Awardee Organization: Awardee Organization: Columbia University Health Sciences, NIH Grant#: 1UG3TR002151-01.

Schuler ML, "Integration of a kidney module into a 4-organ human-on-a-chip system.", Awardee Organization: Hesperos, LLC, NIH Grant#: 1R43DK116589-01.

Edington, Collin D. et al., "Interconnected Microphysiological Systems for Quantitative Biology and Pharmacology Studies", Science Reports, Mar. 14, 2018.

Tsamandouras, N. et al., "Integrated Gut and Liver Microphysiological Systems for Quantitative In Vitro Pharmacokinetic Studies", AAPS J., Sep. 2017.

Lee, H. et al., "A Pumpless Multi-Organ-on-a-Chip (MOC) Combined With a Pharmacokinetic-Pharmacodynamic (PK-PD) Model", Biotechnology and Bioengineering, vol. 114, No. 2, Feb. 2017.

Maass, C. et al., "Establishing Quasi-Steady State Operations of Microphysiological Systems (MPS) Using Tissue-Specific Metabolic Dependencies", Scientific Reports, May 22, 2018.

Sances, S. et al., Human iPSC-Derived Endothelial Cells and Microengineered Organ-Chip Enhance Neuronal Development, Stem Cell Reports, vol. 10, Apr. 10, 2018.

Sebastian Schaaf, Aya Shibamiya, Marco Mewe, Alexandra Eder, Andrea Stöhr, Marc N. Hirt, Thomas Rau, Wolfram-Hubertus Zimmermann, Lenard Conradi, Thomas Eschenhagen, Arne Hansen, Human Engineered Heart Tissue as a Versatile Tool in Basic Research and Preclinical Toxicology, PLoS ONE Oct. 20, 2011 6(10): e26397, https://doi.org/10.1371/journal.pone.0026397.

Caspi O, Lesman A, Basevitch Y, Gepstein A, Arbel G, Habib IH, Gepstein L, Levenberg S., Tissue Engineering of Vascularized Cardiac Muscle from Human Embryonic Stem Cells, Circulation Research Jan. 11, 2007; 100: pp. 263-272.

L. T. Shenje, P. Andersen, M. K. Halushka, C. Lui, L. Fernandez, G. B. Collin, N. Amat-Alarcon, W. Meschino, E. Cutz, K. Chang, R. Yonescu, D. A. S. Batista, Y. Chen, S. Chelko, J. E. Crosson, J. Scheel, L. Vricella, B. D. Craig, B. A. Marosy, D. W. Mohr, K. N. Hetrick, J. M. Romm, L. F. Scott, D. Valle, J. K. Naggert, C. Kwon, K. F. Doheny, D. P. Judge, Mutations in Alstrom Protein Impair Terminal Differentiation of Cardiomyocytes, Nature Communications, Mar. 4, 2014, vol. 5, Article No. 3416.

Li H, Sun S, Liu H, Chen H, Rong X, Lou J, Yang Y, Yang Y, Liu H, Use of a biological reactor and platelet-rich plasma for the construction of tissue-engineered bone to repair articular cartilage defects, Exp. Ther. Med. Aug. 2016, vol. 12(2) pp. 711-719.

Masuda S, Shimizu T, Three-dimensional cardiac tissue fabrication based on cell sheet technology, Adv. Drug Deliv. Rev. Jan. 2016, vol. 96 pp. 103-109.

Ramachandran SD, Schirmer K, Munst B, Heinz S, Ghafoory S, Wolfl S, Simon-Keller K, Marxa Oie CI, Ebert MP, Walles H, Braspenning J, Breitkopf-Heinlein K, In Vitro Generation of Functional Liver Organoid-Like Structures Using Adult Human Cells, PLoS One, Oct. 2015, vol. 10(10) pp. e0139345.

De Peppo GM, Vunjak-Novakovic G, Marolt D, Cultivation of human bone-like tissue from pluripotent stem cell-derived osteogenic progenitors in perfusion bioreactors, Methods Mol. Biol. 2014 vol. 1202 pp. 173-184.

Bhumiratana S, Bernhard JC, Alfi DM, Yeager K, Eton RE, Bova J, Shah F, Gimble JM, Lopez MJ, Eisig SB, Vunjak-Novakovic G, Tissue-engineered autologous grafts for facial bone reconstruction, Sci. Transl. Med. Jun. 2016, vol. 8(343) pp. 343ra83.

Ding M, Henrikesen SS, Wendt D, Overgaard S, An automated perfusion bioreactor for the streamlined production of engineered osteogenic grafts, J. Biomed. Mater. Res. B Appl. Biomate., Apr. 2016,vol. 104(3) pp. 532-537.

Figallo E, Cannizzaro C, Gerecht S, Burdick JA, Langer R, Elvassore N, Vunjak-Novakovic G, Micro-bioreactor array for controlling cellular environments, Lab Chip, Jun. 2007, vol. 7(6) pp. 710-719.

Hansmann J, Groeber F, Kahlig A, Kleinhans C, Walles H., Bioreactors in tissue engineering—principles, applications and commercial constraints. Biotechnol. J., Mar. 2013, 8(3) pp. 298-307.

Wang Z, Kim K., Organ-on-a-Chip Platforms for Drug Screening and Tissue Engineering, Biomedical Engineering: Frontier Research and Converging Technologies, Jan. 2016, pp. 209-233.

The IPRP mailed Sep. 1, 2016 in Application No. PCT/ US2016/031768.

Eschenhagen et al.: "Cardiac tissue engineering.", Transpl. Immunol., vol. 9, No. 2-4, May 2002 (May 1, 2002), pp. 315-321.

Masutani et al.: "Levosimendan restores the positive force-frequency relation in heart failure.", Am J Physiol Heart Circ Physiol., vol. 301, No. 2, Aug. 2011 (Aug. 1, 2011), pp. H488-H49.

Tulloch et al.: "Growth of engineered human myocardium with mechanical loading and vascular coculture.", Circulation Research., vol. 109, No. 1, 2011, pp. 47-59.

Yazawa et al.: "Using induced pluripotent stem cells to investigate cardiac phenotypes in Timothy syndrome.", Nature, vol. 471, No. 7337, Mar. 10, 2011 (Mar. 10, 2011), pp. 230-234.

Shamir and Ewald, "Three-dimensional organotypic culture: experimental models of mammalian biology and disease." Nat Rev Mal Cell Biol. Oct. 2014;15(10):647-64. doi: 10.1038/nrm3873. Epub Sep. 17, 2014. (Year: 2014).

Liau et al. "Pluripotent stem cell-derived cardiac tissue patch with advanced structure and function." Biomaterials. Dec. 2011;32(35): 9180-7 (Year: 2011).

(56) References Cited

OTHER PUBLICATIONS

Ronaldson et al. "P-431: Human iPS Cell Based Cardiac Microtissue Platform for Predictive Toxicity Studies" Tissue Engineering Part A.Dec. 2014. Published in vol. 20 Issue S1: Dec. 3, 2014 (Year: 2014).
Stevens et al. "Physiological function and transplantation of scaffold-free and vascularized human cardiac muscle tissue." Proc Natl Acad Sci U SA. Sep. 29, 2009; 106(39): 16568-16573. (Year: 2009).
The IPRP mailed Sep. 29, 2017 in Application No. PCT/ US2017/041996.
Elisa Cimetta, Elisa Figallo, Christopher Cannizzaro, Nicola Elvassore, and Gordana Vunjak-Novakovic, Microbioreactor arrays for controlling cellular environments: design principles for human embryonic stem cell applications Methods. Feb. 2009 ; 47(2): 81-89.
Meyvantsson I and Beebe DJ, Cell Culture Models in Microfluidic Systems, Annu. Rev. Anal. Chem. 2008, 1:423-49.
Wikswo JP. The relevance and potential roles of microphysiological systems in biology and medicine.Exp Biol Med. Feb. 2014; 239(9) pp. 1061-1072.
Zhang YS. Engineering challenges in microphysiological systems. Future Sci OA. Aug. 2017; 3(3) FSO209.
Low LA and Tagle DA. Microphysiological Systems ("Organs-on-Chips") for Drug Efficacy and Toxicity Testing. Clin Transl Sci. Jul. 2017; 10(4): pp. 237-239.
Ellis BW, Acun A, Can UI, Zorlutuna P., "Human iPSC-derived myocardium-on-chip with capillary-like flow for personalized medicine", Biomicrofluidics, vol. 11/Issue 2, No. 024105, Mar. 2017.
Marsano A, Conficconi C, Lemme M, Occhetta P, Gaudiello E, Votta E, Cerino G, Redaelli A, Rasponi M, "Beating heart on a chip: a novel microfluidic platform to generate functional 3D cardiac microtissues" Lab on a Chip, vol. 16 / Issue 7, pp. 599-610, Feb. 2016.
Aratyn-Schaus Y, Pasqualini FS, Yuan H, McCain ML, Ye GJ, Sheehy SP, Campbell PH, Parker KK, "Coupling primary and stem cell-derived cardiomyocytes in an in vitro model of cardiac cell therapy", The Journal of Cell Biology, vol. 212 / Issue 4, pp. 389-397, Feb. 2016.
Lind JU, Busbee TA, Valentine AD, Pasqualini FS, Yuan H, Yadid M, Park SJ, Kotikian A, Nesmith AP, Campbell PH, Massak JJ, Lewis JA, Parker KK, "Instrumented cardiac microphysiological devices via multimaterial three-dimensional printing", Nature Materials, vol. 16 / Issue 3, pp. 303-308, Mar. 2017.
Zhang YS, Arneri A, Bersini S, Shin SR, Zhu K, Goli-Malekabadi Z, Aleman J, Colosi C, Busignani F, Dell'Erba V, Bishop C, Shupe T, Demarchi D, Moretti M, Rasponi M, Dokmeci MR, Atala A, Khademhosseini A, "Bioprinting 3D microfibrous scaffolds for engineering endothelialized myocardium and heart-on-a-chip", Biomaterials, vol. 110, pp. 45-59, Dec. 2016.
Miklas JW, Nunes SS, Sofia A, Reis LA, Pahnke A, Xiao Y, Laschinger C, Radisic M, "Bioreactor for modulation of cardiac microtissue phenotype by combined static stretch and electrical stimulation", Biofabrication, vol. 6 / Issue 2 No. 024113, Jun. 2014.
Huebsch N, Loskill P, Deveshwar N, Spencer CI, Judge LM, Mandegar MA, Fox CB, Mohamed TM, Ma Z, Mathur A, Sheehan AM, Truong A, Saxton M, Yoo J, Srivastava D, Desai TA, So PL, Healy KE, Conklin BR, "Miniaturized iPS-Cell-Derived Cardiac Muscles for Physiologically Relevant Drug Response Analyses", Scientific Reports, vol. 6, No. 24726, Apr. 2016.
Parker KK, "Human cardio-pulmonary system on a chip", Harvard Medical School, NIH Grant No. 3UH3TR000522-05S1.

\* cited by examiner

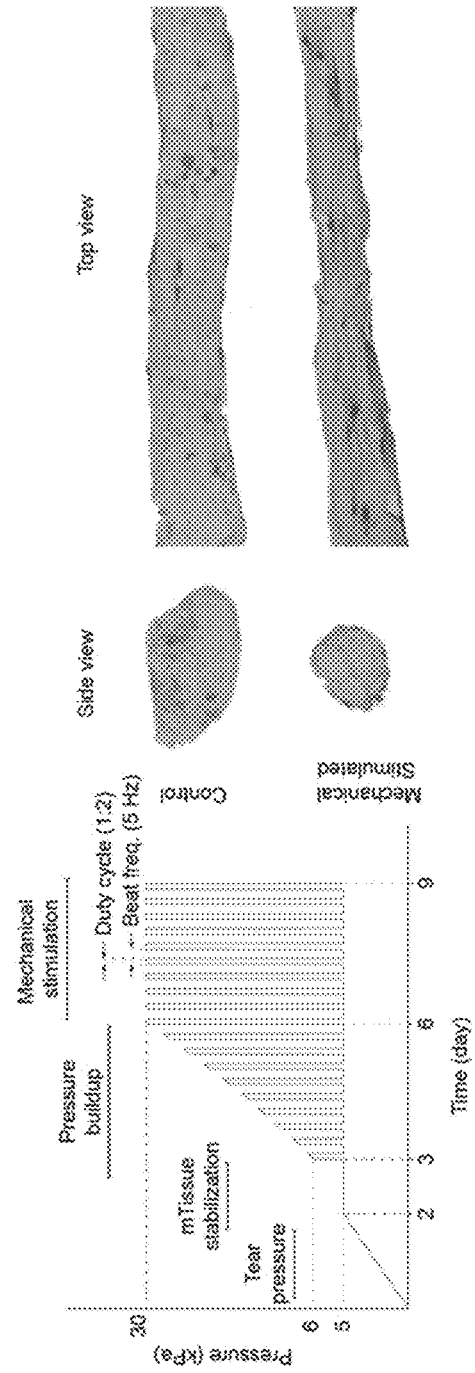

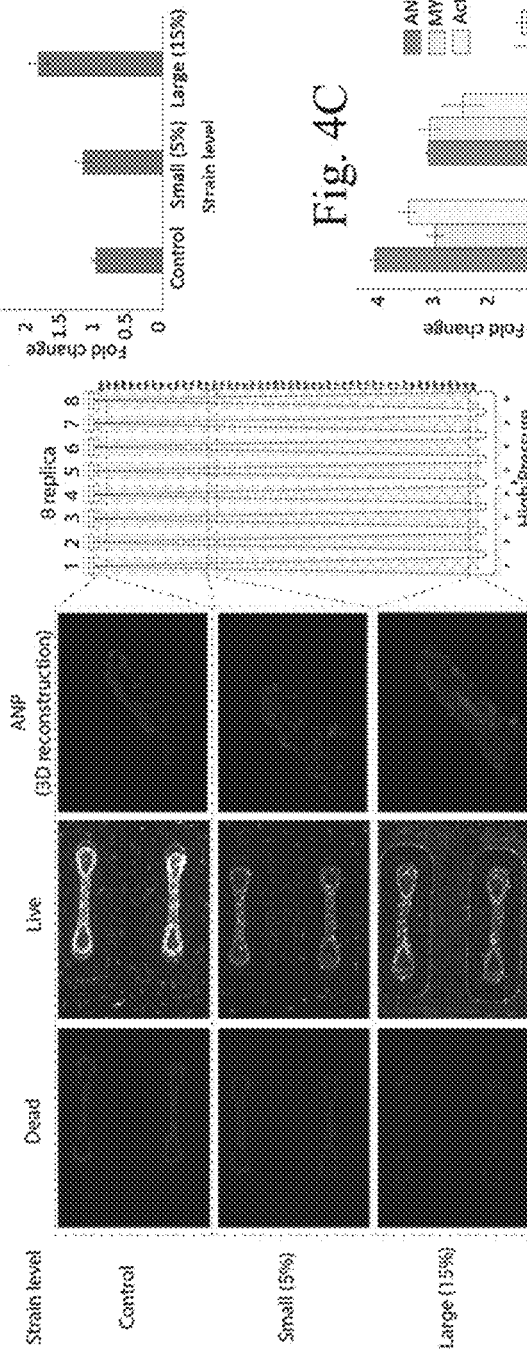
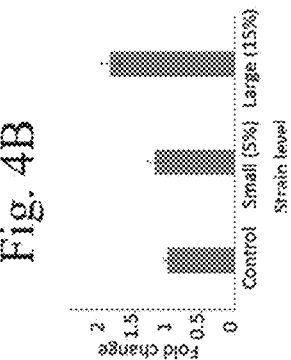
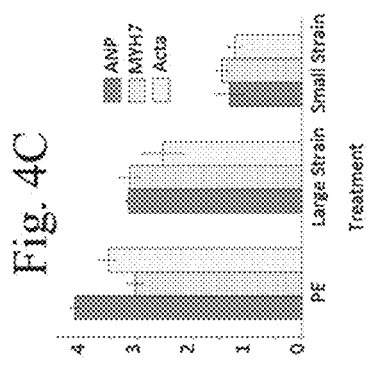
Fig. 4A
Fig. 4B
Fig. 4C

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atctgatgga tttcaagaac c                                            21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctctgagacg ggttgacttc                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaacttgcgc tatcccactc                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctgagggctg gaagtcactc                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
-continued

<400> SEQUENCE: 5
gcaccgcaaa tgcttctagg                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gagagagagc gcgtacacag                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gttaccaggg ctgccttctc                                               20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggtttcccg ttgatgacc                                                19
```

SMART MICRO BIOREACTOR PLATFORM FOR HIGH THROUGHPUT MECHANICAL STIMULATION OF CARDIAC MICROTISSUE

CROSS-REFERENCE TO RELATED APPLICATION

This application claims the benefit of U.S. Provisional Application No. 62/538,014 filed on Jul. 28, 2017 entitled "A SMART MICRO BIOREACTOR PLATFORM FOR HIGH THROUGHPUT MECHANICAL STIMULATION OF CARDIAC MICROTISSUE".

SEQUENCE LISTING

The instant application contains a Sequence Listing which has been submitted electronically in ASCII format and is hereby incorporated by reference in its entirety. Said ASCII copy, created on Oct. 28, 2020, is named 17-50016-US_SL.txt and is 2,171 bytes in size.

STATEMENT OF GOVERNMENT INTEREST

This invention was made with government support under grants HL076485, EB002520, and GM007367 awarded by the National Institutes of Health. The government has certain rights in the invention.

BACKGROUND

Cardiovascular disease remains a global burden, accounting for over 17 million deaths per year worldwide, and this number is predicted to further increase with time. The persistence of abnormal physiological conditions due to cardiovascular disease eventually gives rise to heart failure (HF), and the inability of the heart to adequately pump blood. The hallmark of HF is pathological cardiac hypertrophy, defined as an increase in heart size. Prior to HF, the hypertrophied heart is thought to be a compensatory mechanism against an increased pressure or volume overload, which may allow for normal heart function for many years. However, if the chronic stress is not alleviated, pathological hypertrophy worsens, leading to apoptosis and fibrosis and functional changes such as altered cellular Ca2+ homeostasis, ion channel remodelling, reduced contractile force and relaxation velocity—all which are predisposing factors for arrhythmias and heart failure.

The heart also hypertrophies during sustained exercise and pregnancy. Similar to pathological hypertrophy, physiological hypertrophy is associated with an increase in cardiomyocyte size and structural changes. While traditionally viewed as a favourable adaptation, the small number of sudden cardiac arrest cases in highly trained athletes, as well as the prevalence of peripartum cardiomyopathy imply that physiological hypertrophy may have more in common with its pathological counterpart than it has been previously thought. With such a blurry line between the two types of hypertrophy, understanding the key factors in hypertrophy may aid to the development of new therapies for the treatment of heart failure. Despite considerable efforts, the mechanisms underlying the differences between physiological and pathological hypertrophy remain incompletely understood.

The classical model to study cardiac hypertrophy has been transverse aortic constriction (TAC), in which the afterload of the heart is increased by banding either the thoracic or the abdominal aorta. TAC consistently results in cardiac hypertrophy, while the functional outcomes such as heart failure can vary. Furthermore, this method is labor-intensive and cost-intensive, and does not allow studies of cardiomyocyte biology, a general limitation of in vivo models. Also, it is difficult to differentiate direct load-induced alterations from systemic and humoral mechanisms in this model. Finally, this animal model mimics pressure overload rather than volume overload characteristic of cardiac hypertrophy.

In vitro models of cardiac hypertrophy have been developed to overcome some of the limitations of animal models, such as the use of neonatal rat cardiomyocytes stimulated by α-adrenergic agonists such as Phenylephrine (PE), and mechanically stimulated monolayers cultured on stretchable silicone membranes. But these too also have their limitations and at times fail to recapitulate native biology, reducing the value of experimental data. For example, cardiomyocytes in cell culture are often isotropic, whereas cardiomyocytes in heart tissue are highly aligned and organized. Also, standard 2D monolayer cell cultures do not allow measurement of contractile function, an important parameter differentiating physiological from pathological hypertrophy.

Thus, a high-throughput, physiologically accurate model for studying cardiac hypertrophy induced by volume overload is needed to make up for the experimental model deficiency. The present disclosure describes a platform that recapitulates some critical aspects of native three-dimensional (3D) structure and function of the heart tissue. Of relevance to practical applications, the design and operation of this system allow testing of thousands of loading conditions using only minimal resources.

SUMMARY

The present disclosure relates to an improved micro-bioreactor system that addresses the deficiencies in the art. In one embodiment, the micro-bioreactor comprises a tissue culture layer defining a plurality of culture wells. Each culture well comprises a first pillar and a second pillar each extending vertically from the floor of the culture well. These first and second pillars are separated by a distance and are aligned along a central axis traversing the width of the culture well. In one aspect, the first and second pillars may have a cross-sectional tear shape to facilitate tissue attachment. The micro-bioreactor further comprises a pressure control layer disposed beneath the tissue culture layer. The pressure control layer defines a plurality of channels with each channel underlying a group of the plurality of culture wells. This group of culture wells is aligned along the channel, wherein the channel has a first width at a first end and tapers progressively to a second width at a second end. As such, the channel width underlying each culture well of the group is different. The pressure control layer further comprises an access port for communicating a pressurized gas to the plurality of channels. In this way, each culture well in the group is exposed to a different pressure based on the channel width underlying each culture well.

In certain embodiments, the micro-bioreactor further comprises a pressure regulator in communication with the access port for providing the pressurized gas to the plurality of channels.

In any of the above embodiments, the micro-bioreactor may comprise from about 500 to about 1000 culture wells.

In any of the above embodiments, the distance separating the first and second pillars is from 300 μm to about 700 μm, from about 400 μm to about 600 μm, from about 500 μm to about 600 μm, or from about 300 μm to about 500 μm. The height of each of the first and second pillars may be from about 100 µm to about 300 µm.

In any of the above embodiments, the width of the culture well may be from about 1,500 µm to about 2,100 µm, and the length of the culture well may be from about 500 µm to about 700 µm.

In any of the above embodiments, the tissue culture layer and pressure control layer comprises polydimethylsiloxane (PDMS). The PDMS may comprise a Poisson's ratio of from about 0.35 to about 0.55, and more preferably 0.45. The PDMS may comprise a Young's Modulus of form about 0.5 MPa to about 5 MPa, and more preferably about 2.3 MPa. The concentration of PDMS is preferably higher in the tissue culture layer than in the pressure control layer.

The present disclosure also provides for a method for culturing and testing microtissues using the micro-bioreactors described herein is also provided. The method comprises the following steps:

(a) mixing a plurality of cells with an extracellular matrix (ECM) material to form a cell-ECM culture mixture;

(b) applying oxygen plasma to the culture wells;

(c) loading samples of the cell-ECM culture mixture into a desired number of culture wells overlying at least one of the channels of the pressure control layer;

(d) removing any portion of the sample of the cell-ECM culture mixture not contained entirely in the culture wells;

(e) incubating the micro-bioreactor under conditions sufficient to permit cross-linking of the ECM material;

(f) applying culture media to the culture wells;

(g) culturing the cell-ECM culture mixture under conditions sufficient to permit formation and maturation of a microtissue that extends around and between the first and second pillars of each well; and (h) applying pressure to the pressure control layer from a single pressure regulator via the access port, said pressure sufficient to cause the channel to bulge thereby leading to horizontal displacement of the first and second pillars away from each other, wherein the extent of horizontal displacement is dependent on the width of the channel underlying each culture well.

In any of the above embodiments, the samples of the cell-ECM culture mixture may comprise from about 300 cells to about 700 cells and more preferably about 500 cells.

In any of the above embodiments, the cells may be cardiomyocytes or a mixture of cardiomyocytes and cardiac fibroblasts.

In any of the above embodiments, the pressure applied may be 30 kPa at a frequency of 5 Hz.

In any of the above embodiments, the ECM material may be a collagen gel.

In any of the above embodiments, the conditions sufficient to permit cross-linking may be 37° C. for 5 minutes.

In any of the above embodiments, the conditions sufficient to permit formation and maturation of the microtissue may comprise an environment of 5% CO2 and 37° C. for a period of 72 hours.

BRIEF DESCRIPTION OF THE DRAWINGS

FIG. 2A provides phase-contrast images of the micro-bioreactor.

FIG. 2B provides simulated images of µbiorator in the unstretched state and under pressure (top and side views).

FIG. 2C depicts finite element analysis results to predict strain level as the function of control layer dimension and input pressure using COMSOL Multiphysics.

FIG. 2D provides experimental data for the two cases of varying channel length and input pressure (3 cases each).

FIG. 3A depicts a regimen for high-throughput mechanical stimulation of µtissues.

FIG. 3B depicts H&E staining of stimulated and control µtissues.

FIGS. 4A-4C provide data related to dose-dependent hypertrophic response.

FIG. 4A depicts comparison of viability and ANP expression of the three points on the gradient with nonexistent, small and large strain levels (0, 5% and 15%).

FIG. 4B depicts ANP level characterization

FIG. 4C depicts atrial natriuretic peptide (ANP), cardiac myosin heavy chain beta (MHC-β), and alpha skeletal muscle actin (ACTA1) gene expression level for small and large strain level compared to the non-stimulated µtissues. PE-stimulated µtissues served as positive control for hypertrophy.

DETAILED DESCRIPTION

The present disclosure provides a high throughput µbioreactor that can be used to model cardiac hypertrophy associated with volume overload on the heart, by pneumatic (non-contact) loading of cardiac tissues. Using this system, it is possible to study the effects of mechanical stress on cardiac hypertrophy, by real-time, on-chip analysis of the tissue phenotype.

The bioreactor assembly involves fabrication of two separate layers from, for example, PDMS, and partially curing the bottom layer such that they can be aligned and then subsequently cured together. Cells are induced to fuse into µtissues around elastic pillars. By incorporating a novel control layer, pneumatic channels underneath the µwells are pressurized, deflecting the pillars and subjecting the tissues to mechanical stress. The soft lithography techniques permit custom design channel widths. When calibrated, these custom-sized channels allow each individual µwell to be subjected to a specific predetermined strain.

Figure 5:
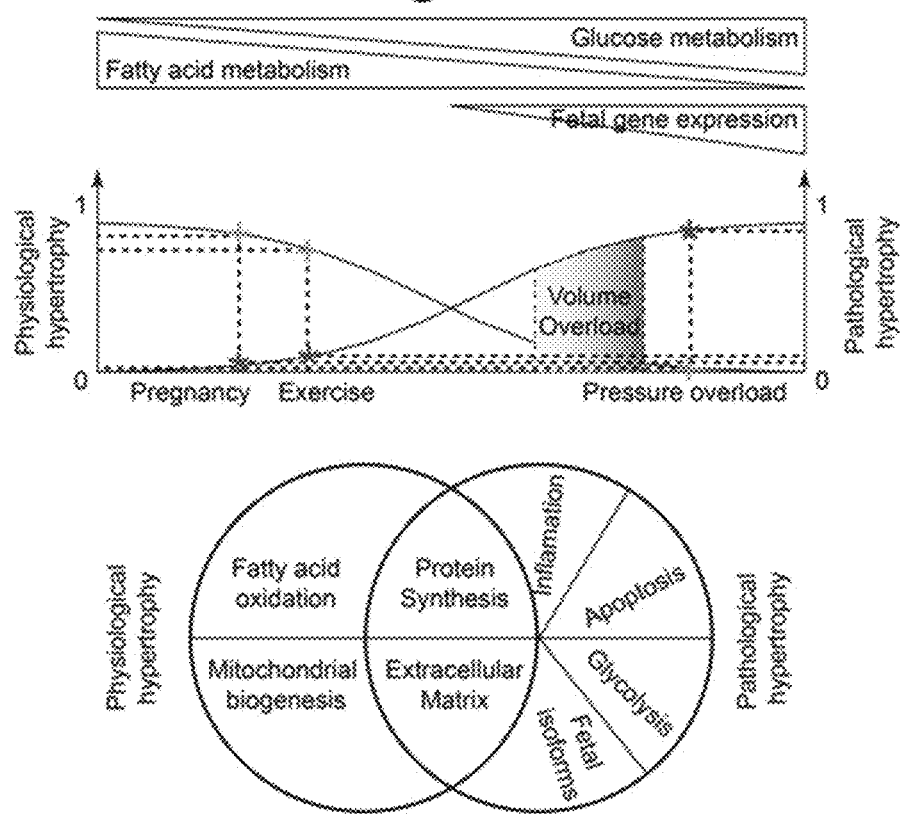
FIG. 5 provides a logical continuum of physiological and pathological hypertrophy.

To demonstrate the utility of the device, the gene expression profiles of cardiac tissues subjected to a gradient of mechanical stress were measured. Hypertrophic markers were found to be upregulated in a dose-dependent manner at both the small and large strains. The same trend of change was observed in pathological markers, without significant increases in apoptosis, such that a clear distinction between pathological or physiological hypertrophy could not be established. It is possible that intermediate levels exist between the normal and pathologically hypertrophied hearts, that could be characterized for how physiological they are (FIG. 5).

The microfluidic platform provides the ability to mimic the increased mechanical stresses present in volume overload, and study, in a high throughput fashion, the regimens which may contribute to hypertrophy being more or less physiologic in nature. The present approach may be useful in recognizing the adaptive and potentially maladaptive features of "physiological" hypertrophy, and to better appreciate the possibilities of harnessing various aspects of physiological hypertrophy in therapeutic modalities for the heart failure.

The micro-bioreactors (μbioreactors) of the present disclosure are fabricated using soft lithography techniques, to facilitate quick formation of large numbers of structurally organized cardiac μtissues in a desired geometry. The μbioreactors are a high-throughput non-contact device that can regulate the development of μtissues formed from very small numbers of cells (only 500 per μtissue), under conditions favoring the formation of functional cardiac muscle, and providing mechanical stimulation without extraneous setup. The multilayer μbioreactor platform of the present disclosure comprises a tissue culture layer, and a pneumatically actuated control layer.

Figure 1B:
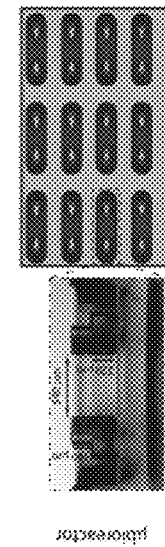
FIG. 1B provides a schematic of the bioreactor platform with an array of µbioreactors for large scale production of cardiac µtissues along with the cross-sectional view.
Figure 1C:
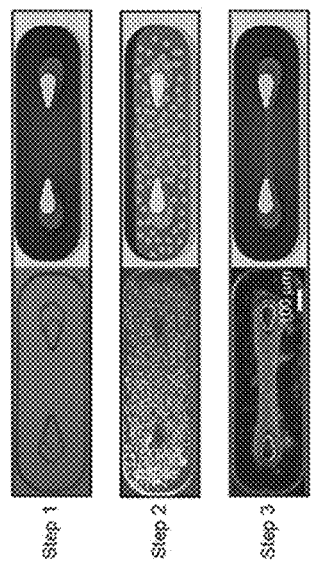
FIG. 1C provides a schematic and images of the cardiac µtissue formation; Step 1) µbioreactor oxygen plasma treatment Step 2) mixture cell-ECM (5M cell/mL in collagen gel at density of 2 mg/mL) loaded in the well (0.1 µL/well). Step 3) the mixture of cell-ECM compacts around the pillars allowing the alignment of cardiomyocytes and maturation of the cardiac µtissue.
Figure 1A:
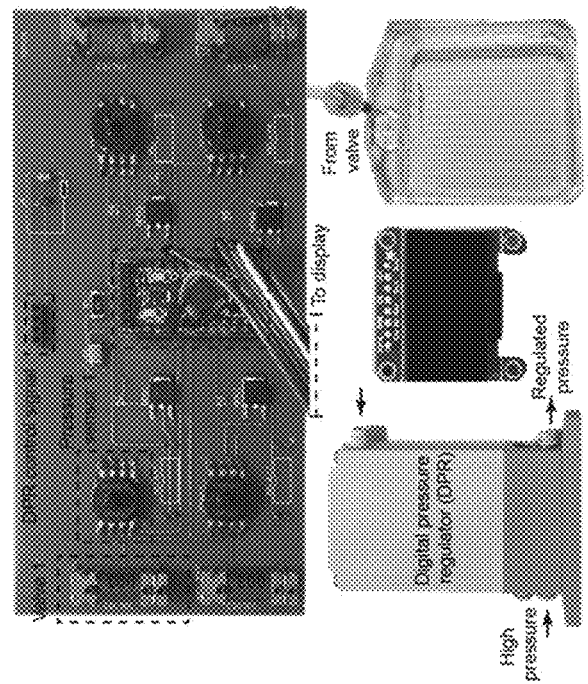
FIG. 1A provides a pictoral representation of a custom-designed electronic circuitry (including a digital pressure regulator, display, 4 miniature solenoid valves, 4 pressure sensors, 4 relays, etc.) to control 4 bioreactors independently.

In an exemplary embodiment, the culture layer is 580 μm thin, and contains 900 μbioreactor wells, organized as a 18×50 matrix, with μwells spaced 300 μm apart from each other. Each μwell measures 1,800 μm×600 μm, and is 400 μm deep. Centered in each μwell are two 180 μm tall pillars standing 540 μm apart. The control layer underneath the culture layer consists of linear channels, and is pressurized by compressed air to deflect the thin culture layer, and stretch the μtissue. The pressure in the control layer is set and maintained by a digital pressure regulator that can be turned on and off at the desired frequency, via pneumatic valves. By calibrating the width of the pneumatic channels, each μbioreactor can be individually loaded, perfused, and monitored (using phase-contrast or fluorescence microscopy), in real time (FIGS. 1A-1C).

In one embodiment, the two-layer device is constructed using different ratios of the curing agent and PDMS for the culture layer and the control layer (1:7 and 1:15 ratios, respectively). This allows for tight bonding with the adhesive strength of up to 60 kPa, and for unlimited time to achieve perfect alignment between layers. Second, in order to further strengthen the bonding between the two layers, the control layer is partially cured before bonding by precisely adjusting the baking time until it retains both the physical shape and initial adhesive quality. The control layer is fully cured under compression after the alignment with the culture layer. Lastly, since PDMS is air-permeable, a 5% CO2-95% air mixture at 37° C. can be used to maintain the culture media pH.

Cells cultured in 3D collagen gels form a syncytial network that can be mechanically loaded. Mechanical loading of cells encapsulated in ECM matrix is more desirable because in tissues both the cells and their matrix bear strain, which in turn significantly alters gene expression profiles. The steps of μtissue generation are outlined for a single μbioreactor in FIG. 1C. After inoculation of cell suspension in ECM into each μbioreactor (only 0.1 μL of cell suspension is required), cells constrict the hydrogel around the μ-pillars, and self-organize into an aligned tissue.

Cardiomyocytes remodel their matrix by eliminating water, and by reorganizing and aligning the collagen fibrils. This process is scaled up for the entire bioreactor platform (containing 900 μbioreactors) by placing the cell-ECM mixture over the PDMS construct and scraping off the excess using the dialysis membrane, such that the cell-ECM mixture is retained within each μbioreactor. To ensure μtissue formation, prior to the cell-ECM transfer, the bioreactor surface is made hydrophilic by plasma treatment.

EXAMPLES

The following Examples are intended to illustrate the advantages and features of one particular embodiment of the present micro-bioreactor system. The Examples therefore should not be interpreted as the only operable embodiment as various design specifications of the microbioreactor could be modified to support various other applications yet still apply the inventive concepts described herein.
Materials and Methods
Functional Design and Computational Analysis 3D modeling of the bioreactor was performed using Solidworks software (Solidworks Corp.). This model was imported into the finite element analysis software COMSOL Multiphysics. Using the Solid Mechanics Module, we modelled the deflection of the pillars due to the application of different pressures in the fluidic channel. Based on the modelling results, the design was modified in an iterative fashion. The material properties of PDMS used to fabricate the bioreactor were as follows: Poisson's ratio=0.45, Young's Modulus=2.3 MPa. A fixed boundary condition was applied to the base of the object bonded to the well plate. The default stationary solver was used to solve the finite element model.

Device Design and Fabrication

The master was designed using AutoCAD (Autodesk). SU-8 masters were fabricated by patterning layers of SU-8 photoresist (Microchem) onto the 4" silicon wafers through successive spin coat, alignment, exposure, and bake steps. Constructs of PDMS (Sylgard 184, Dow Corning) were molded from the master by mixing base to curing agent (1:7 and 1:15 for the culture and control layers respectively) and curing at 65° C. In order to achieve specific thickness in the culture layer we spun-coat PDMS (1:7 ratio) on the master at 165 rpm for 60 s, followed by baking at 65° C. for 10 min. PDMS at 1:15 ratio was then used to replica-mold the control layer and bake it at 65° C. for 28 min while continuously monitoring its curing. Baking was stopped before the control layer was completely cured, and the two layers were aligned such that the control layer channels were parallel to each other underneath the culture layer wells. We fabricated an alignment device to precisely position the control layer atop the culture layer before baking (Supplementary information). Through this method, we achieved robust performance of the device at operating pressures as high as 60 kPa, and perfect alignment. After alignment, the assembly was returned to the oven, this time under compression for full curing and attachment (4 hr at 75° C.). Then the bonded layers were peeled off the culture layer master and the surrounding walls were molded from PDMS (1:10 ratio), and subsequently cured in the oven. Prior to tissue culture, devices were sterilized using the autoclave.

Finally, a hole is punched through the mold and into the control layer. Silicone tubing was inserted to pressurize the control layer. In order to extend the life of the device for multiple uses, EtO sterilization was used.

After device fabrication and in order to test our design parameters and validate the simulation results, we imaged the device (top-view) undergoing pressure-induced stretch.

The horizontal displacement of the pillars was quantified through ImageJ software for multiple values of control pressures and geometries.

Neonatal Cardiomyocyte Isolation

Neonatal rat hearts (n=20, postnatal day 0-3: P0-P3) were dissociated using Neonatal Heart Dissociation Kit (Miltenyi Biotec GmbH 130-098-373) following manufacturer instructions. The single cell suspension was enriched with cardiomyocytes using the Neonatal Cardiomyocytes Isolation Kit (Miltenyi Biotec GmbH 130-105-420). Cardiomyocytes were isolated by depletion of non-target cells. First, non-target cells were directly magnetically labelled with a cocktail of monoclonal antibodies conjugated with MACS® MicroBeads. Then, the cell suspension was loaded onto a MACS Column, which is placed in the magnetic field of a MACS Separator. The magnetically labelled non-target cells were retained within the column, while the unlabelled cardiomyocytes run through.

µTissue Culture

Isolated cardiomyocytes were mixed with cardiac fibroblasts at the ratio of 10:1 and encapsulated in collagen gel (2.5 mg/mL), at a density of 12 million cells/ml. Constructs were treated with oxygen plasma for 2 min to reduce the hydrophobicity of PDMS. 250 µl of cell-ECM mixture was evenly distributed. A dialysis membrane was gently and uniformly laid over the construct using sterile tweezers. By raking a cell scraper over the membrane, excess gel was firmly but carefully removed. This is a critically important step because cells growing outside of the wells may exert forces on the µtissues. This step also ensured entry of the gel into the µwells without generating air bubbles. After placing the construct into the incubator at 37° C. for 5 min to crosslink the collagen gel, a small amount of media (2 ml) was pipetted over the top of the membrane to prevent dehydration of the cells. To remove the membrane, media was added into the well until the membrane was completely submerged, and the device was again placed in the incubator for another thirty minutes. After soaking in the media for 10-30 min, the membrane automatically dissociated from the surface of the device and was collected using sterile tweezers. Following washing the leftover cell-ECM mixture using sterile 1× phosphate buffered saline (PBS), fresh medium was added and cells were cultured for 3 days until full tissue maturation.

Live-Dead Assay

After 6 days of mechanical stimulation (or control culture), µtissues were incubated in DMEM medium containing 2 µM Calcein and 4 µM of ethidium homodimer-1 for 30 min at 37° C., 5% CO2, as indicated by the manufacturer's protocol (LIVE/DEAD® Viability/Cytotoxicity Kit, Molecular Probes). Samples were imaged under a fluorescence microscope (Olympus IX81 light microscope, Center Valley Pa.).

Histology and Immunofluorescence

The µtissues were fixed in 4% formaldehyde for 15 min in situ. For H&E staining liquid paraffin is poured in the mold. After cooling to room temperature, the whole paraffin block was released from the flexible PDMS mold containing the array of µtissues and processed for cross sectional sectioning and staining. For immunofluorescence staining, the whole µtissue was incubated in 1% BSA/10% normal goat serum/0.3M glycine in 0.1% PBS-Tween for 1 h in situ to permeabilize the cells and block non-specific protein-protein interactions after fixing. The cells were then incubated with the primary antibody ab40791 at 1/200 dilution overnight at +4° C. The secondary antibody (far red) was Goat Anti-Rabbit IgG H&L (Alexa Fluor® 680), at a 1/500 dilution for 1 h. Then the samples were imaged using broadband confocal microscope (Leica TCS SP5 MP).

Quantitative Real-Time PCR (qRT-PCR)

Total RNA from µtissues was obtained using RNAqueous®-Micro Total RNA Isolation Kit (Life Technologies) following the manufacturer's instructions. RNA preparations were treated with "Ready-to-go you-prime first-strand beads" (GE Healthcare) to generate cDNA. Quantitative real-time PCR was performed using DNA Master SYBR Green I mix (Applied Biosystems). mRNA expression levels were quantified applying the ΔΔCt method. First, the difference between the Ct values (ΔCt) of the gene of interest and the housekeeping gene was calculated for each experimental sample. Then, the difference in the ΔCt values between the experimental and control samples ΔΔCt was calculated. The fold-change in expression of the gene of interest between the two samples was calculated as $2\sqrt{(-\Delta\Delta Ct)}$. The primers used were: ANP, sense: 5'-ATCTGATGGATTTCAAGAACC-3' (SEQ ID NO: 1), antisense: 5'-CTCTGAGAC GGGTTGACTTC-3' (SEQ ID NO: 2); MYH7, sense: 5'-GAACTTGCGCTATCCCACTC-3' (SEQ ID NO: 3), antisense: 5'-CTGAGGGCTGGAAGTCACTC-3' (SEQ ID NO: 4); Acta, sense: 5'-GCA CCGCAAATGCTTCTAGG-3' (SEQ ID NO: 5), antisense: 5'-GAGAGAGAGCGCG TACACAG-3' (SEQ ID NO: 6); and GAPDH, sense: 5'-GTTACCAGGGCTGCCTTCTC-3' (SEQ ID NO: 7), antisense: 5'-GGGTTTCCCGTTGATGACC-3' (SEQ ID NO: 8).

Results

Strain Characterization

The engineered µtissue was successfully stretched with our novel stimulation system (FIGS. 2A-2D). By pressurizing the fluidic channel, pillars in the top layer of the device are pushed apart. We then set out to achieve the main advantage of our platform, which is the mechanical loading of each µtissue at any desired strain. While this could have been achieved by changing the pressure, it would have required 900 individual digital pressure regulators (DPRs). In order to avoid this setback, we developed fluidic channels of variable width in the control layer. This allows us to subject each of the 900 µtissues to a unique strain level using a single DPR.

Figure 2A:
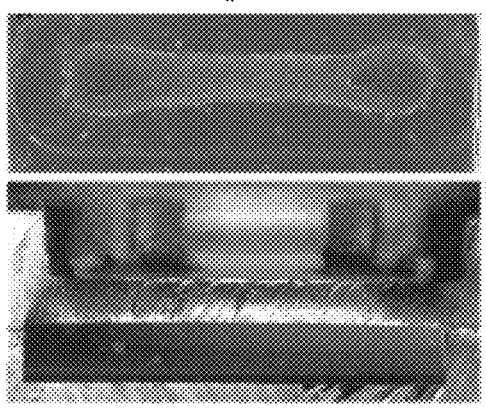
FIG. 2A-2D provide pictoral representations and data relating to application of mechanical stimulation of the micro-bioreactor of the present disclosure.
Figure 2B:
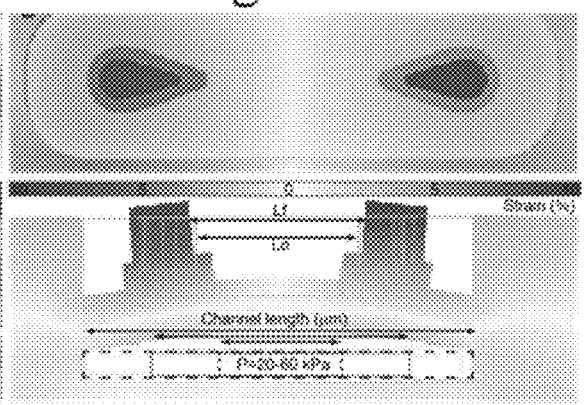
Figure 2C:
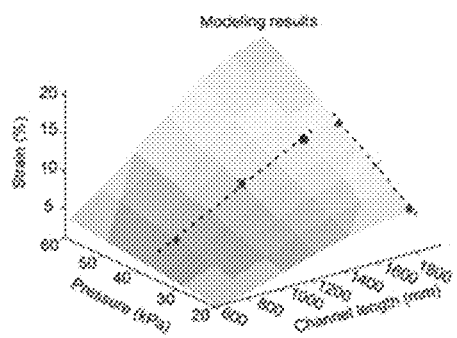
Figure 2D:
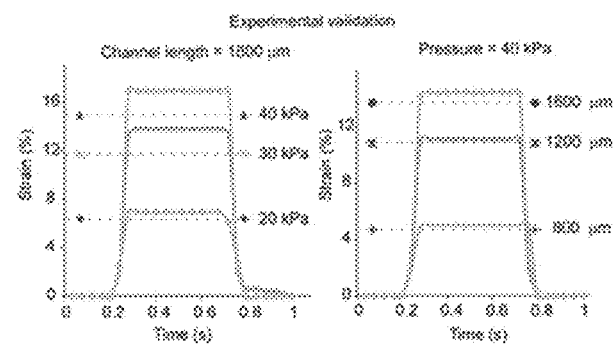

In order to characterize the degree of strain imposed on each the µtissues, we used finite element analysis (COMSOL Multiphysics, FIG. 2C). Image analysis of the displaced pillars over the course of one stimulation period confirmed the simulation results (FIG. 2D).

Mechanical Stimulation of the µTissues

After 3 days of pre-culture that was necessary to form cell-hydrogel constructs, µtissues were subjected to mechanical stimulation. The desired pressurization of the underlying fluidic channel was accomplished via an actuation circuitry. The silicone tubing sealed into the control layer was connected to the actuator containing a simple microcontroller that opened and closed a valve at the desired frequency when pressurized. To avoid damage to the tissue and to allow the cells to adjust to their microenvironment, the stimulation regimen contained an initial tare load applied slowly. For rat cardiomyocytes, we applied a beat frequency of 5 Hz and a pressure of 30 kPa to apply 10% strain, a regimen based on previous work with a frequency to match the native beating of the rat heart. It is conceivable that the stimulation frequency and duty cycle will be adjusted for each cell source origin (e.g., human). The collagen fibers aligned over time, in the direction of stretch (FIG. 3B).

Dose-Dependent Hypertrophic Response

The relationship between the mechanical stimulation regimen and the hypertrophic response was investigated. To this end, we incorporated the underlying microfluidics containing tapered channels (FIG. 4A, right). In this way, a gradient of strain was applied to μtissues, which were then subject to real-time analysis. We sought to determine if there is a relationship between the stimulation gradient and the hypertrophic response.

First, we confirmed that different levels of mechanical stimulation were not affecting the viability of the μtissues. FIG. 4A (first two columns) compares cell viability at three points across the gradient with no strain, low strain and large strain (0, 5% and 15%). Live/dead staining indicates no increase in cell death with increasing strain, while we observed a dose-dependent increase in the atrial natriuretic peptide (ANP) expression, a key marker for cardiac hypertrophy. Moreover, gene expression for ANP, cardiac myosin heavy chain beta (MHC-β), and alpha skeletal muscle actin (ACTA1), which are upregulated in pathological hypertrophy, also revealed a dose-dependent response. In fact, the large-strain group recapitulated the expression profile of cells treated with phenylephrine, a pharmacological agent inducing hypertrophy.

What is claimed is:

1. A micro-bioreactor comprising:
    a tissue culture layer defining a plurality of culture wells, each culture well comprising a first pillar and a second pillar each extending vertically from the floor of the culture well, wherein the first and second pillars are separated by a distance and are aligned along a central axis traversing the width of the culture well, and wherein the first and second pillars each have a cross-sectional tear shape; and
    a pressure control layer disposed beneath the tissue culture layer, the pressure control layer defining a plurality of channels, each channel underlying a group of the plurality of culture wells, wherein the group is aligned along the channel, wherein the channel has a first width at a first end and tapers progressively to a second width at a second end such that channel width underlying each culture well of the group is different, and wherein the pressure control layer comprises an access port for communicating a pressurized gas to the plurality of channels such that each culture well in the group is exposed to a different pressure based on the channel width underlying each culture well.

2. The micro-bioreactor of claim 1 further comprising a pressure regulator in communication with the access port for providing the pressurized gas to the plurality of channels.

3. The micro-bioreactor of claim 1, wherein the plurality of culture wells is from about 500 to about 1000 culture wells.

4. The micro-bioreactor of claim 1, wherein the distance separating the first and second pillars is from 300 μm to about 700 μm.

5. The micro-bioreactor of claim 1, wherein the distance separating the first and second pillars is from 400 μm to about 600 μm.

6. The micro-bioreactor of claim 1, wherein the distance separating the first and second pillars is from 500 μm to about 600 μm.

7. The micro-bioreactor of claim 1, wherein the depth of the culture well is from about 300 μm to about 500 μm.

8. The micro-bioreactor of claim 1, wherein the width of the culture well is from about 1,500 μm to about 2,100 μm.

9. The micro-bioreactor of claim 1, wherein the length of the culture well is from about 500 μm to about 700 μm.

10. The micro-bioreactor of claim 1, wherein the height of each of the first and second pillars is from about 100 μm to about 300 μm.

11. The micro-bioreactor of claim 1, wherein the tissue culture layer and pressure control layer comprises polydimethylsiloxane (PDMS).

12. The micro-bioreactor of claim 11, wherein the PDMS comprises a Poisson's ratio of from about 0.35 to about 0.55.

13. The micro-bioreactor of claim 11 wherein the PDMS comprises a Young's Modulus of from about 0.5 MPa to about 5 MPa.

14. The micro-bioreactor of claim 11, wherein the concentration of PDMS is higher in the tissue culture layer than in the pressure control layer.

15. The micro-bioreactor of claim 12, wherein the PDMS comprises a Poisson's ratio of 0.45.

16. The micro-bioreactor of claim 13, wherein the PDMS comprises a Young's Modulus of about 2.3 MPa.

\* \* \* \* \*